(12) United States Patent
Honda et al.

(10) Patent No.: US 10,307,176 B2
(45) Date of Patent: Jun. 4, 2019

(54) MEDICAL DEVICE AND MEDICAL DEVICE ASSEMBLY

(71) Applicant: TERUMO KABUSHIKI KAISHA, Tokyo (JP)

(72) Inventors: Kei Honda, Hadano (JP); Takehisa Mori, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 559 days.

(21) Appl. No.: 14/868,984

(22) Filed: Sep. 29, 2015

(65) Prior Publication Data

US 2016/0089171 A1  Mar. 31, 2016

(30) Foreign Application Priority Data

Sep. 30, 2014 (JP) ................. 2014-201665

(51) Int. Cl.
*A61B 17/22* (2006.01)
*A61B 17/221* (2006.01)
(Continued)

(52) U.S. Cl.
CPC ............ *A61B 17/221* (2013.01); *A61B 17/22* (2013.01); *A61B 2017/00553* (2013.01); *A61B 2017/00561* (2013.01); *A61B 2017/22079* (2013.01); *A61B 2017/320775* (2013.01); *A61B 2217/005* (2013.01)

(58) Field of Classification Search
CPC ............ A61B 17/221; A61B 17/22031; A61B 17/32056; A61B 17/22; A61B 2017/2212–2017/2217; A61B 2017/22079; A61B 2017/22034–2017/22035; A61B 2017/00553; A61B 2017/00561; A61F 2/01–2/013; A61F 2002/011–2002/018
See application file for complete search history.

(56) References Cited

U.S. PATENT DOCUMENTS 5,569,275 A * 10/1996 Kotula ........... A61B 17/320758
606/159
5,989,266 A  11/1999 Foster
(Continued)

FOREIGN PATENT DOCUMENTS

JP  2001-512355 A  8/2001
WO  WO 98/36694 A1  8/1998

*Primary Examiner* — Darwin P Erezo
*Assistant Examiner* — Jonathan A Hollm
(74) *Attorney, Agent, or Firm* — Buchanan Ingersoll & Rooney PC

(57) ABSTRACT

A medical device for collecting a solid object together with a fluid in a living body, including: a cylindrical member having an inner cavity, a suction port provided on the distal end of the inner cavity, and a discharge port on a side wall and communicating with the inner cavity; an impeller in the inner cavity configured to carry the fluid from the suction port to the discharge port; and a filter in the inner cavity configured to collect the solid object. At least part of the wall surface of the cylindrical member, which defines a flow channel allowing movement of the fluid from the impeller to the discharge port, is inclined from a center axis of the cylindrical member toward a distal end with respect to a transverse direction of the cylindrical member.

23 Claims, 8 Drawing Sheets

(51) Int. Cl.
  *A61B 17/00* (2006.01)
  *A61B 17/3207* (2006.01)

(56) References Cited

U.S. PATENT DOCUMENTS 6,080,170 A * 6/2000 Nash .................. A61B 17/22
                                            606/159
2007/0135832 A1 * 6/2007 Wholey .............. A61F 2/013
                                            606/200

* cited by examiner

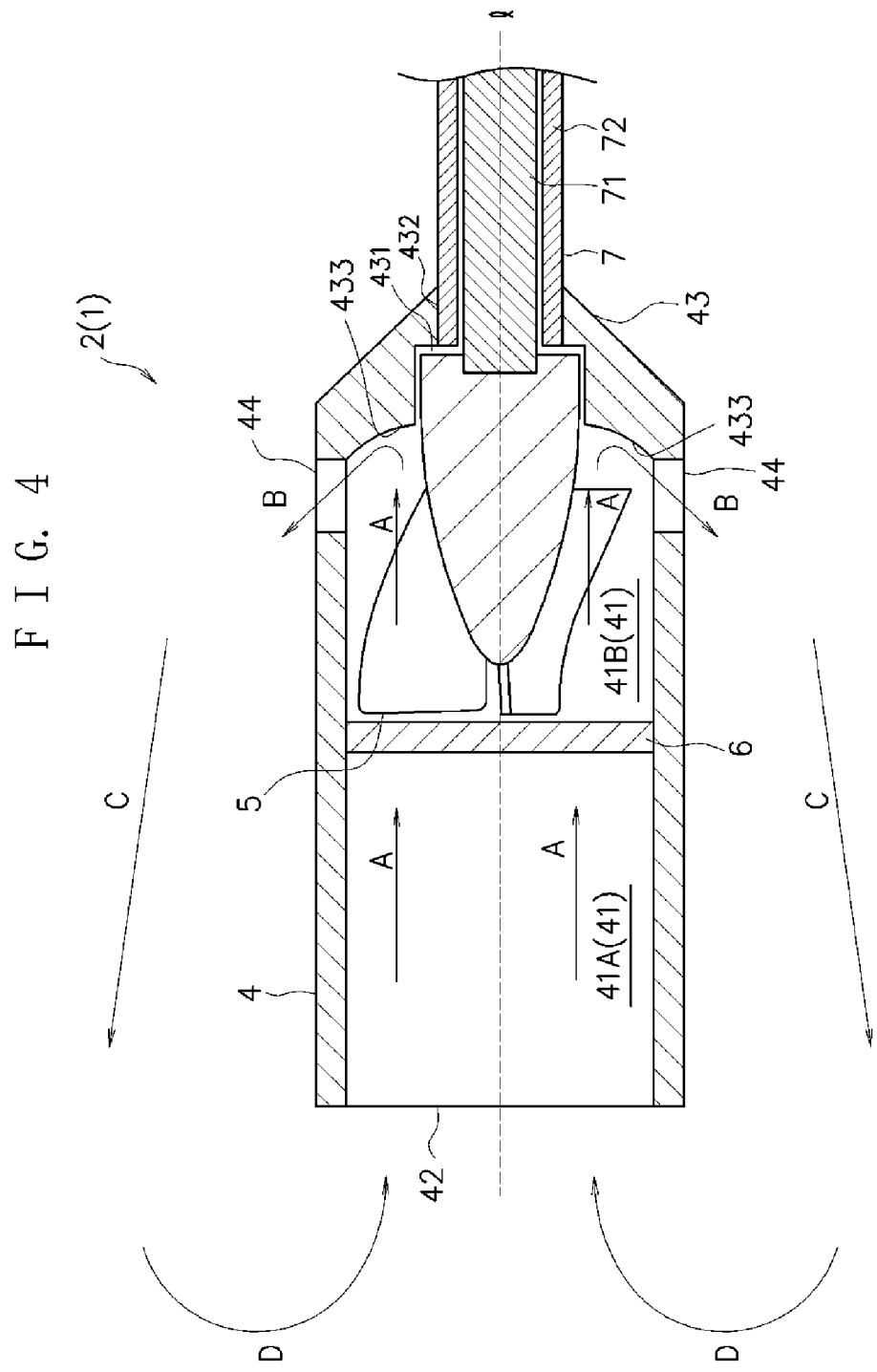

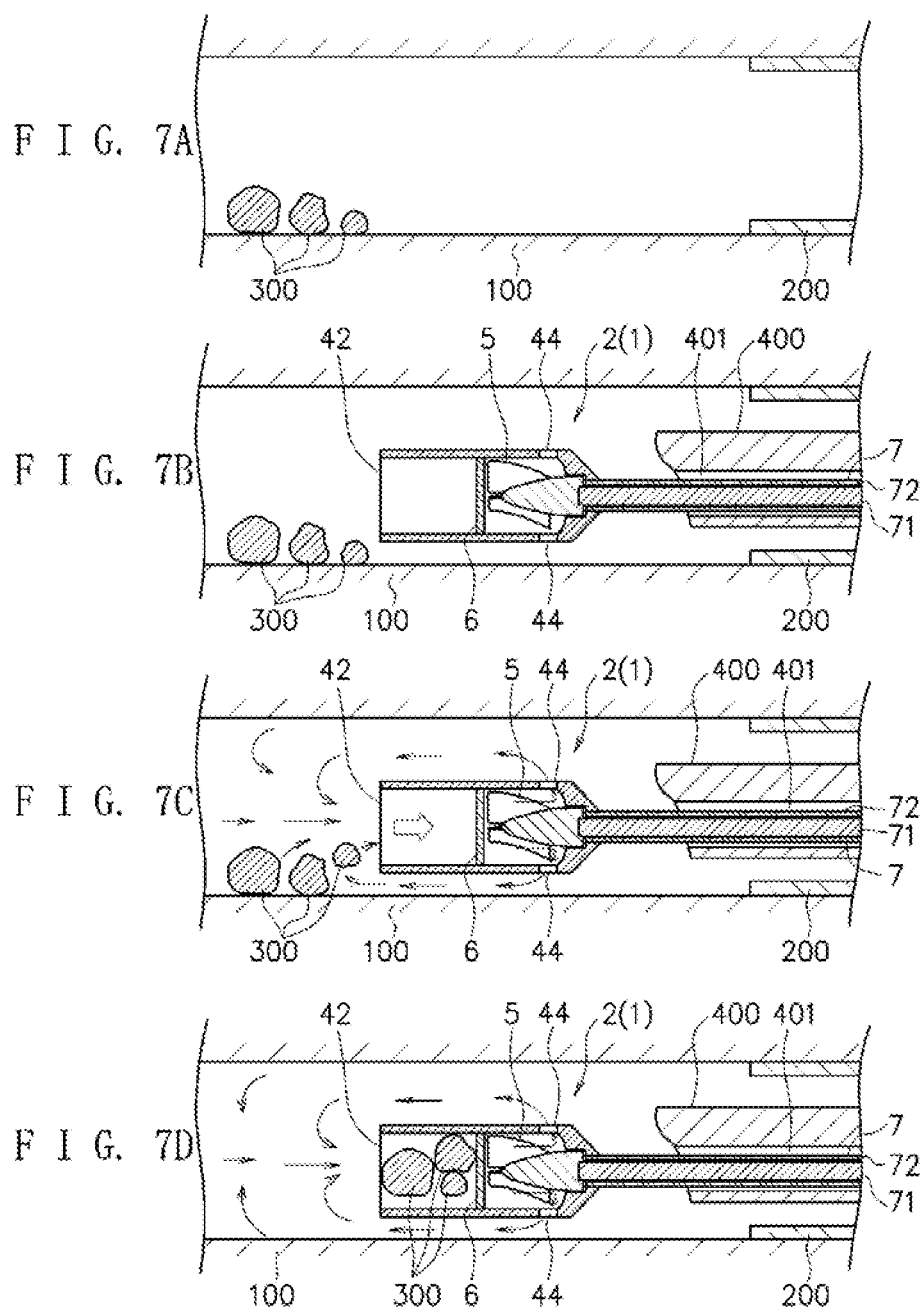

MEDICAL DEVICE AND MEDICAL DEVICE ASSEMBLY

This application is based on and claims priority to Japanese Application No. 2014-201665 filed on Sep. 30, 2014, the entire content of which is incorporated herein by reference.

FIELD OF THE INVENTION

The present invention relates to a medical device and a medical device assembly.

BACKGROUND DISCUSSION

Urinary tract stones include calculi existing in a urinary tract such as a kidney, a ureter, a bladder, a urethra and the like. A calculus generated in a kidney or in a ureter is referred to as an upper urinary tract stone. In urinary tract stone disease, various symptomatic states are caused by these urinary tract stones. For example, when a calculus generated in a kidney is moved to a ureter, the calculus injures the ureter and causes a pain or blood in the urine. The calculus may also block the ureter, so that an evanescent hydronephrosis state is generated, and hence an acute pain (colic pain) from a lower back to a lateral region may result. Therefore, in order to alleviate or treat these symptoms, removal of the calculi is considered to be effective.

Among methods of removing calculi existing in an upper urinary tract, a transurethral ureterolithotripsy (TUL or URS), an extracorporeal shock wave lithotripsy (ESWL), and a percutaneous calculus lithotripsy (PCNL or PNL) are known as a surgical positive method of removal. Examples of the TUL include an r-TUL (or r-URS) in which a rigid uretero-reno fiberscope (or a rigid ureteroscope) is used, and an f-TUL (or f-URS) in which a flexible uretero-reno fiberscope (or a flexible ureteroscope) is used. Among these methods, the TUL generally is a therapeutic approach using an uretero-reno fiberscope (or an ureteroscope), and including reaching calculi existing in a ureter or renal pelvis and renal calyx extracorporeally, transvesically, or ureterily, directly breaking the calculi, and extracting the stones. The TUL has a higher stone free rate in comparison with ESWL or PCNL, and gives less damage to the ureter, thereby having an advantage of being less invasive. In particular, such an advantage is significant in the f-TUL.

In the TUL, stone breaking and extraction of the stones are performed via an instrument channel of the rigid ureteroscope or the flexible ureteroscope. The stone breaking is generally performed by using a laser fiber such as Holmium: YAG (Ho:YAG) laser or the like. The extraction of the stones is generally performed by using a basket catheter (basket forceps). Known examples of the basket catheter include a medical instrument as disclosed in JP-T-2001-512355.

However, the extraction of the stones using the basket catheter of the related art is limited by the gripping function of the basket catheter, the size of a ureteral inner cavity or the size of a ureteral access sheath (guiding catheter). Hence, only a small amount of the calculus and calculi broken pieces can be removed at one time. Often removal requires a series of stone extracting operations to remove the pieces one by one, from a step of gripping the broken calculus pieces to a step of carrying the gripped broken calculus pieces to the outside of the body with the basket catheter. Therefore, in order to remove the calculus, it is necessary to perform an insertion and retraction operation of the basket catheter many times between the outside of the body and the position where the calculus exists. Accordingly, a user (operator) bears a heavy burden. In addition, various disadvantages for a patient occurs due to an elongation of an operation time for performing the insertion and retraction operation of the basket catheter many times such as an increased probability of infection of the urinary tract after the operation or the like, a development of burden to a ureter due to ischemia or the like, and an increased risk of relapse because of a failure of removal of the calculi and the broken calculus pieces within a limited time of operation set for suppressing infection or the like following a surgical procedure.

The basket catheter used in the related art generally has a difficulty to grip calculi or broken pieces having small diameters. In contrast, a basket catheter developed for collecting the small diameter calculi or broken pieces generally has difficulty gripping calculi having large diameters, causing insufficient operability. In addition, a method of breaking calculi or the broken pieces into sand-like diameters (i.e., very small pieces) so that natural stone drainage by a urine flow is expected is proposed. However, this method requires labor and time for breakage and, in addition, requires preparation of a specific laser output apparatus in many cases. Therefore this method is not practical and cost-effective for widespread use at the moment.

The basket catheter has difficulty collecting the calculi and broken pieces which are located positions difficult for the forceps to access, such as corners of minor calyx, side of renal papilla or the like. Consequently, in the method of the related art using the basket catheter, it is difficult to improve the stone free rate, and is difficult to reduce the relapse rate.

In addition, by gripping a plurality of calculi and the broken pieces, end surfaces of the calculi are exposed by a gap between the metallic wires that are part of the basket forceps. Therefore, if an attempt is made to remove the plurality of calculi and the broken calculus pieces to the outside of the body at once, inner walls or the like of the kidney and the ureter may become damaged. Another problem arises when exposed portions of the calculi fit into (i.e., are lodged in) an end surface of an opening of an ureteral access sheath on a far side and hence cannot be pulled out to the outside of the body. In such a case, the basket catheter is forced to be discarded.

SUMMARY

In view of such problems identified above, the medical device disclosed here is capable of efficiently collecting solid objects having small diameters in a living body and solid objects existing in narrow portions in the living body. Another aspect of the disclosure here is a method of collecting the solid objects in the living body using the medical device.

In order to solve the problems described above, the present inventors have found that the solid objects having small diameters in the living body, the solid objects existing in narrow portions in the living body, and a plurality of solid objects in the living body can be collected by sucking the solid objects in the living body and collecting them with a filter. The inventors also found that a suction force is improved by forming a circulating flow using a fluid (for example, perfusate) sucked together with the solid objects and using the perfusate for suction, so that a collecting efficiency is improved.

In other words, the invention relates to the following:

(1) A medical device for collecting an existing solid object together with a fluid in a living body, including:

a cylindrical member having an inner cavity, a suction port provided on a far end side of the inner cavity, and a discharge port arranged on a side surface and communicating with the inner cavity;

an impeller arranged in the inner cavity and configured to carry the fluid from the suction port to the discharge port; and a filter arranged in the inner cavity and configured to collect the solid object, wherein at least part of a wall surface which defines a flow channel which allows a movement of the fluid from the impeller to the discharge port is inclined from a center axis of the cylindrical member as an original point toward a far end side with respect to a transverse direction of the cylindrical member.

(2) The medical device according to a description (1), wherein the cylindrical member includes a wall portion traversing the inner cavity on a near end side of blades of the impeller, and the wall portion is inclined from the center axis of the cylindrical member as an original point toward the far end side with respect to the transverse direction of the cylindrical member.

(3) The medical device according to a description (1) or (2), wherein the wall portion and part of a side wall which defines the discharge port are integrated and form an identical plane.

(4) The medical device according to a description (3), wherein at least part of the side wall is inclined from the center axis of the cylindrical member as an original point toward the far end side with respect to the transverse direction of the cylindrical member.

(5) The medical device according to any one of the descriptions (1) to (4), wherein an opening of the discharge port on an outer surface side of the cylindrical member has a width in a circumferential direction of the cylindrical member on the far end side is larger than the width on the near end side.

(6) The medical device according to any one of the descriptions (1) to (5), wherein an opening of the discharge port on the inner cavity side faces a near end of the blade of the impeller.

(7) The medical device according to any one of the descriptions (1) to (6), wherein the impeller is a screw.

(8) The medical device according to any one of the descriptions (1) to (7), wherein a fluid discharged from the discharge port moves in a direction toward the far end of the cylindrical member to form a circulating flow passing through the inner cavity during the operation of the impeller.

(9) A medical device assembly for collecting an existing solid object together with a fluid in a living body, including:

a medical device, the medical device including:

a cylindrical member having an inner cavity, a suction port provided on a far end side of the inner cavity, and a discharge port arranged on a side surface and communicating with the inner cavity;

an impeller arranged in the inner cavity and configured to carry the fluid form the suction port to the discharge port;

a filter arranged in the inner cavity and configured to collect the solid object; and a drive shaft coupled to the impeller and configured to transmit a drive force to the impeller, wherein at least part of a wall surface which defines a flow channel which allows a movement of the fluid from the impeller to the discharge port is inclined from a center axis of the cylindrical member as an original point toward a far end side with respect to a transverse direction of the cylindrical member, and a drive unit coupled to the drive shaft and configured to provide the drive shaft with the drive force.

(10) A method of collecting an existing solid object together with a fluid in a living body, including:

providing a medical device having: a cylindrical member having an inner cavity, a suction port provided on a far end side of the inner cavity, and a discharge port arranged on a side surface and communicating with the inner cavity; an impeller arranged in the inner cavity and configured to carry the fluid from the suction port to the discharge port; and a filter arranged in the inner cavity and configured to collect the solid object, wherein at least part of a wall surface which defines a flow channel which allows a movement of the fluid from the impeller to the discharge port is inclined from a center axis of the cylindrical member as an original point toward a far end side with respect to a transverse direction of the cylindrical member, inserting the medical device into the living body and arranging the suction port near the solid object, and activating the impeller, sucking the solid object together with the fluid into the inner cavity, and collecting the solid object by using a filter.

According to the configuration described, a medical device may collect solid objects having small diameters in a living body, solid objects in narrow portions in the living body, and efficiently collect a plurality of solid objects. Another aspect of the disclosure here is a method of collecting the solid objects in the living body using the medical device.

In particular, since at least part of a wall surface which defines a flow channel allowing a movement of the fluid from an impeller to a discharge port is inclined from a center axis of a cylindrical member as an original point toward a far end side with respect to a transverse direction of the cylindrical member, a circulating flow passing through the cylinder is stably generated during the operation of the impeller. Consequently, when sucking is performed in the narrow portions, the fluid can always be supplied to the narrow portions, so that sucking in the narrow portions may be continuously performed without depletion of the fluid.

BRIEF DESCRIPTION OF THE DRAWINGS

FIG. 4 is a cross-sectional view of an operation of the medical device assembly illustrated in FIG. 1;

FIGS. 7A to 7D are explanatory schematic drawings of a preferred embodiment of a method of the invention.

DETAIL DESCRIPTION

Referring now to the attached drawings, the medical device, medical device assembly and method disclosed here will be described in detail below on the basis of preferred embodiments.

First of all, a medical device and a medical device assembly according to the preferred embodiments of the invention will be described.

Figure 1:
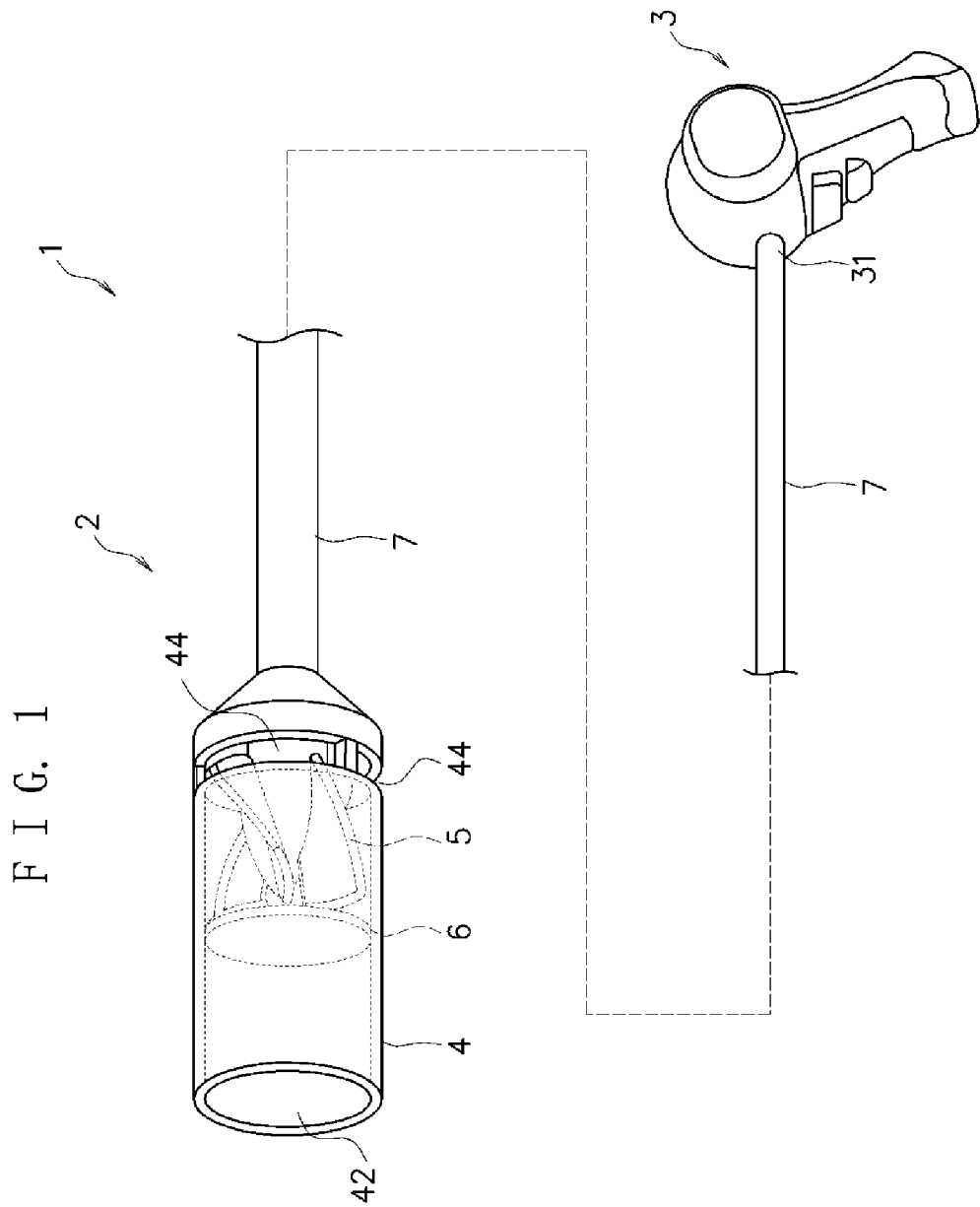
FIG. 1 is a schematic drawing of a medical device assembly according to a preferred embodiment of the invention.
Figure 2:
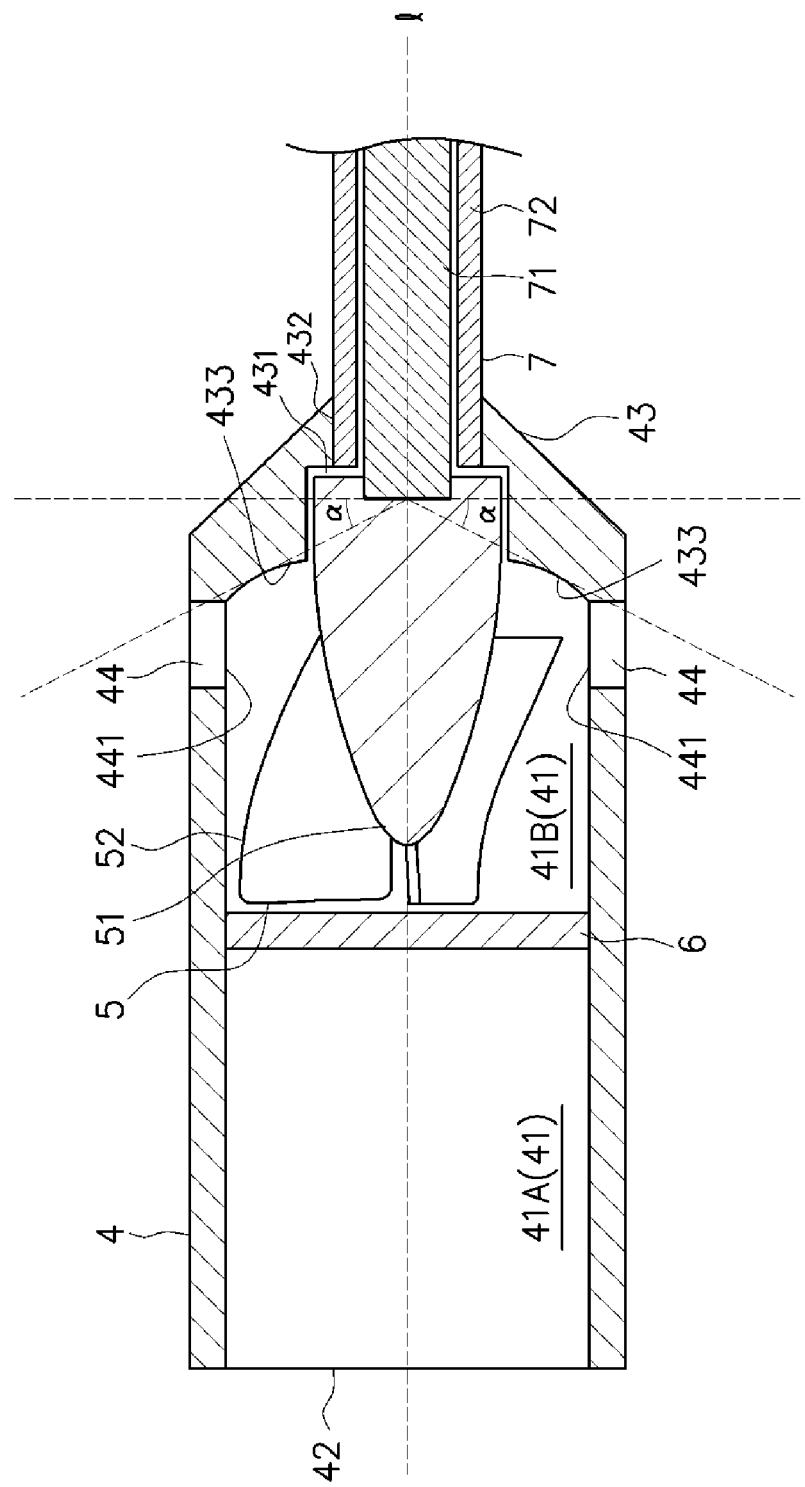
FIG. 2 is a cross-sectional view of a medical device provided in the medical device assembly illustrated in FIG. 1.
Figure 3:
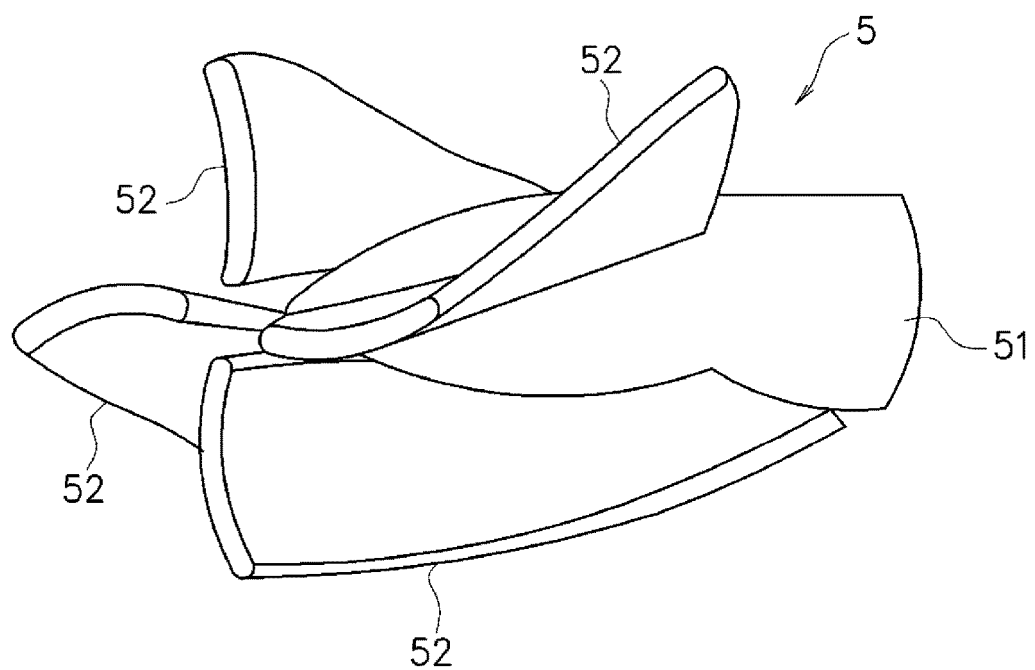
FIG. 3 is a perspective view of an impeller provided in the medical device assembly illustrated in FIG. 1.

FIG. 1 is a schematic drawing of the medical device assembly according to the preferred embodiment of the invention. FIG. 2 is a cross-sectional view of the medical device provided in the medical device assembly illustrated in FIG. 1. FIG. 3 is a perspective view of an impeller provided in the medical device assembly illustrated in FIG. 1. FIG. 4 is a cross-sectional view of an operation of the medical device assembly illustrated in FIG. 1. In the respective drawings of this application, the sizes of the respective members are exaggerated as needed for the sake of simplifying the description, and the illustrated members do not indicate the actual sizes. In the following description, the term "distal end" means the "far end", and the term "proximal end" means the "near end". The near end is the side of the medical device assembly 1 closer to an operator when the operator uses the medical device assembly 1. The far end is the side of the medical device 1 farther from the operator when the operator uses the medical device assembly 1.

The medical device assembly 1 illustrated in FIG. 1 includes a medical device 2 and a drive unit 3, and is an assembly formed of a combination of the medical device 2 and the drive unit 3. The medical device assembly 1 is used for collecting an existing solid object together with a fluid in a living body.

A portion in the living body to which the medical device assembly 1 can be applied is not specifically limited, and includes, for example, arbitrary body cavities, inner cavities, and lumens of living ducts in the living body.

Examples of the body cavity, the inner cavity, and the lumen include inner cavities in organs, inner cavities of living ducts, and also a pericardial space, a peritoneal space, a pleural space and the like existing in a urinary system, a cardiovascular system, a respiratory system, a gastrointestinal system, a reproduction system, an endocrine system, a nerve system, a sensory system and the like, although not the disclosure here is not limited to these examples.

Specific examples, particularly examples of the organs and the living ducts of the urinary system, include a ureter, a urethra, a kidney (renal pelvis, renal calyx), a bladder and the like. Other living ducts include, although are not limited to, blood vessels, an esophagus, other digestive tracts, a windpipe, a bile duct, lymph vessels, a vagina and the like. In addition, specific examples of organs include cholecyst or the like, although the organs are not limited to this example.

The solid object in the living body includes one or more solid objects which are to be removed from the living body. The solid object is not specifically limited to a solid, and may include a mixture of a gel-like solid, liquid and/or gas, or the like. Examples of foreign substances include blood clots, various types of calculi such as gallstones, kidney stones, ureter stones, bladder stones, and urethra stones, and sputum.

The medical device assembly 1 can be used as an alternative of a basket catheter, and hence is suitable for removal of solid objects for which the basket catheter is generally used, such as blood clots and various calculi as described above, and kidney stones and urinary tract stones associated with urinary tract stone disease.

Examples of the fluid existing together with the solid object include gas such as air, oxygen, carbon dioxide, nitrogen and the like, various types of liquids, mixtures of gas and liquid, gel, and the like. Examples of the types of liquid include bodily fluid such as blood, tissue water, digestive fluid, saliva, urine, bodily secretion, infiltration fluid and the like, and perfusate, saline, buffer solution, water, bacteriostatic fluid, antiseptic solution, cleaning fluid, sterilization fluid and the like. The medical device assembly 1 forms (i.e., introduces) a circulating flow of a fluid and uses the circulating flow for sucking the solid objects as described below. Therefore, liquid having a smaller density change with respect to the pressure in comparison with gas and a viscosity relatively smaller than the gel (i.e., relatively less compressible and relatively less viscous) is preferable as the fluid.

As illustrated in FIG. 1, the medical device 2 includes a cylindrical member 4, an impeller 5, a filter 6, and a shaft portion 7.

As illustrated in FIG. 1 and FIG. 2, the cylindrical member 4 is a cylindrical member having an inner cavity 41 and includes an opening as a suction port 42 at a distal side of the inner cavity 41, and an opening on a proximal side is covered with a wall portion 43 traversing the inner cavity 41 of the cylindrical member 4.

As illustrated in FIG. 2, the inner cavity 41 formed of the cylindrical member 4 is partitioned by the filter 6 to create a space 41A on the distal side and a space 41B on the proximal side. The filter 6 is in the vicinity of the center of the cylinder in the axial direction of the cylinder, and is further described below. The space 41A on the distal side has the suction port 42 on the distal side of the space 41A, and allows passage of the fluid sucked into the suction port 42, and storage of the solid objects. The space 41B is a space defined by an inner wall surface of the cylindrical member 4, the filter 6 and the wall portion 43. The space 41B stores (i.e., houses) the impeller 5.

The cylindrical member 4 includes three discharge ports 44 on its side surface configured to communicate with the inner cavity 41. The discharge ports 44 allow discharge of the fluid sucked from the suction port 42 and passed in the inner cavity 41 of the cylindrical member 4.

The discharge ports 44 are rectangular through holes arranged equidistantly along the circumferential direction of the cylindrical member 4. In this manner, equidistant arrangement of the discharge ports 44 along the circumferential direction of the cylindrical member makes the fluid uniformly flow in the circumferential direction of the cylindrical member 4 when the fluid is released from the cylindrical member 4.

The wall portion 43 is provided on the proximal side of the cylindrical member 4 described above, i.e., on the proximal side with respect to blades 52 of the impeller 5. The wall portion 43 traverses the inner cavity 41, and forms a bottom portion of the cylindrical member 4 (i.e., the wall portion 43 extends from the proximal end of the discharge ports 43 towards the center axis 1 of the cylindrical member 4). With the wall portion 43 configured as illustrated in FIG. 2, transfer of the fluid sucked into the cylindrical member 4 to the shaft portion 7 side is alleviated (i.e., lessened).

The wall portion 43 has a depression 431 at its center to store (i.e., house or contain) a proximal side of a shaft 51 of the impeller 5. A through hole 432 is formed in the vicinity of the center of the depression 431, and the cylindrical member 4 is coupled to the shaft portion 7 described later at the through hole 432. The proximal side of the shaft 51 of the impeller 5 is stored (i.e., housed or contained) in the depression 431 to stabilize the rotation of the impeller 5 about the center axis 1 of the cylindrical member 4.

The wall portion 43 is inclined from the center axis 1 of the cylindrical member 4 as a starting point so that an inclined portion 433 on the inner cavity 41 extends toward the distal side over the circumferential direction with respect to the transverse direction of the cylindrical member 4, so that the part of the inner wall surface forms an acute angle with the center axis of the cylindrical member (i.e., the wall portion 43 has a smaller diameter at its proximal end and increases in diameter in the distal direction, so that the wall portion 43 extends to the side surface of the cylindrical member 4). In the drawing, an inclination angle α is shown. The fluid flow transferred by the impeller 5 to the proximal side is guided by the inclined portion 433 so that the fluid flow changes direction towards the outer periphery of the cylindrical member 4 and towards the distal side of the cylindrical member to proceed to the discharge ports 44 (i.e., the fluid pushed by the impeller 5 contacts the inclined portion 433 to become redirected distally and radially outwardly in order to be discharged through the discharge ports 44). Therefore, the fluid flow discharged from the discharge ports 44 is capable of proceeding toward the distal side of the cylindrical member 4, so that the circulating flow described later can be formed easily.

In addition, the inclination of the inclined portion 433 toward the distal side changes continuously so as to increase from the center axis 1 of the cylindrical member 4 as it goes toward the outer periphery. Consequently, the inclined portion 433 of the wall portion 43 forms an annular bowl. Accordingly, the inclined portion 433 guides smooth fluid flow and, formation of the circulating flow is easily achieved.

The inclined portion 433 is connected to the discharge ports 44 at the outer peripheral end portion of the discharge ports 44. Accordingly, the flow guided by the inclined portion 433 can be transferred directly to the discharge ports 44 without contact with other members of the medical device 2 or the like.

The discharge ports 44 are arranged so that openings 441 on the inner cavity 41 side face the proximal ends of the blades 52 of the impeller 5. In other words, the discharge ports 44 are arranged so that the proximal ends of the blade 52 are positioned between the distal end and the proximal end of the opening 441 with reference to an axial direction of the cylindrical member 4. Accordingly, in comparison with the case where the proximal ends of the blades 52 exist in the vicinity of the distal end of the opening 441 with reference to the axial direction of the cylindrical member 4, a fluid flow formed in the vicinity of the proximal ends of the blades 52 is not a flow in a direction perpendicular to the axial direction of the cylindrical member 4, but a flow substantially toward the distal side of the cylindrical member 4. Therefore, the flow from the blade 52 perpendicular to the axial direction of the cylindrical member 4 is discharged from the discharge ports 44, and is mixed with the fluid flow discharged from the discharge ports 44 so as to be guided by the inclined portion 433 and proceed toward the distal side of the cylindrical member 4, so that the fluid flow toward the distal side of the cylindrical member 4 is prevented from being blocked (i.e., fluid flow from the discharge ports 44 towards the proximal end of the medical device is minimized so that the overall fluid flow after leaving the discharge ports 44 will be toward the distal end of the cylindrical member). Consequently, the fluid flow toward the distal end of the cylindrical member 4 from the blades 52 is stable, so that the circulating flow which will be described later is also stable (i.e., the flow is relatively less turbulent).

An outer diameter of the cylindrical member 4 described above is not specifically limited, and may be set as needed according to the portion and the object in the living body to which the device is applied. For example, when the medical device 2 is used for the therapy of the urinary tract stone disease, the outer diameter of the cylindrical member 4 preferably allows the passage of a ureteral access sheath and, specifically, 1 to 10 mm is preferable and 3.6 to 4 mm is more preferable.

An inner diameter of the cylindrical member 4 is not specifically limited and may be set so as to collect foreign substances (e.g., solid objects). For example, when the medical device 2 is used for the therapy of the urinary tract stone disease, the inner diameter of the cylindrical member 4 is sized to collect the calculi and/or broken pieces of the calculi. Specifically, 1 to 10 mm is preferable and 2.6 to 3.8 mm is more preferable.

The volume of the space 41A defined by the cylindrical member 4 and the filter 6 is not specifically limited, and has preferably a size which can store a sufficient amount of solid objects and, may be for example, 1 to 2000 $mm^3$, preferably 7 to 80 $mm^3$.

The impeller 5 is arranged in the space 41A on the proximal side with respect to the filter 6 within the inner cavity 41. The impeller 5 has the shaft 51 having an axis of rotation in the axial direction of the cylindrical member 4 and four blades 52 arranged in the circumferential direction of the shaft 51. The impeller 5 rotates about the axis of rotation to generate a fluid flow from the distal side of the cylindrical member 4 toward the proximal side and, consequently transfers the fluid from the suction port 42 to the discharge ports 44.

As illustrated in FIG. 3, the shaft 51 of the impeller 5 has a column-shaped body having a reduced diameter on the distal side, and has a bullet shape as a whole.

The blades 52 are four plate-shaped members arranged equidistantly in the circumferential direction at the distal side of the shaft 51, i.e., in this embodiment, at 90° intervals in the circumferential direction.

The blades 52 are rectangular plate-shaped members having a long-axis direction along the direction of the axis of rotation. The blades 52 each have a long-axis direction twisted in the direction of rotation from the distal side to the proximal side so as to generate a flow in the direction of the axis of rotation by the rotation of the impeller 5. The blades 52 are equal in length and are curved in the direction opposite to the direction of rotation as it goes toward the outer periphery about the axis of rotation (i.e., each blade is curved from the distal end to the proximal end), whereby the impeller 5 constitutes a propeller-type screw as a whole.

The screw (impeller) 5 stabilizes the fluid flow as an axial flow (i.e., fluid flow in the axial direction of the cylindrical member 4), and hence is advantageous for generating the fluid flow from the distal side toward the proximal side of the cylindrical member 4. This axial fluid flow is advantageous for generating a circulating flow passing through the inner cavity 41 of the cylindrical member 4.

As illustrated in FIG. 2, the shaft 51 of the impeller 5 is coupled to a drive shaft 71, which will be described later, on the proximal side of the drive shaft 71. A rotational force (i.e., drive force) of the impeller 5 is obtained via the drive shaft 71.

The filter 6 is arranged within the inner cavity 41 of the cylindrical member 4 so that a main surface of the filter 6 is perpendicular to the axial direction to partition the inner cavity 41 into the space 41A and the space 41B. The filter 6 allows passage of the fluid and prohibits the passage of the solid objects. Accordingly, the solid objects moving together with the fluid transferred from the suction port 42 to the discharge ports 44 are caught by the filter 6 and may be collected.

The filter 6 is not specifically limited as long as it allows passage of the fluid and prohibits the passage of the solid objects. For example, a combination of one or two types or more of textile fabrics (woven fabric, knitted fabric), fiber material (meshed fabric) having a predetermined mesh such as a non-woven fabric or the like, a porous film or the like may be used. Specifically, the meshed fabric having relatively uniform openings is preferably used (i.e., openings that are uniformly spaced and uniformly sized).

The openings of the meshed fabric or average hole diameter of the porous film is not specifically limited, but is preferably 0.01 to 500 µm and, more preferably 20 to 200 µm.

The shaft portion 7 includes the elongated drive shaft 71 and a sheath 72 that covers the drive shaft 71.

The distal end of the drive shaft 71 is configured to pass through the through hole 432 of the cylindrical member 4 to couple with the proximal end of the shaft 51 of the impeller 5. The proximal end of the drive shaft 71 is demountably mounted to a drive unit 3 as described below. A drive force (rotational force) generated by the drive unit 3 is transmitted to the impeller 5.

The distal end of the sheath 72 is fixed to the through hole 432 at the proximal end of the cylindrical member 4, and the proximal end of the sheath 72 is configured to be demountably mountable to the drive unit 3.

The effective length of the shaft portion 7 is not specifically limited, but must be long enough to send the cylindrical member 4 to an intended affected area. Specifically, the effective length of the shaft portion 7 is preferably 20 to 150 cm, and more preferably 65 to 120 cm.

The outer diameter of the shaft portion 7 is not specifically limited, and is preferably small enough to pass through an instrument channel of a microscope, for example. Specifically, the outer diameter of the shaft portion 7 is preferably 0.1 to 3 mm and more preferably, 0.3 to 1.2 mm.

The drive unit 3 illustrated in FIG. 1 includes a casing and a driving apparatus stored in the casing. The casing is shaped to allow the operator to grip the casing, and is provided with various units for controlling the driving apparatus. In other words, the drive unit 3 also serves as operating unit of the medical device assembly 1.

The drive unit 3 may be coupled to the proximal end of the shaft portion 7 at a coupling unit 31, and is capable of connecting the drive shaft 71 and the driving apparatus. By activating the driving apparatus, the drive force (rotational force) is transmitted to the impeller 5 via the drive shaft 71, so that the medical device 1 can be activated. Examples of the driving apparatus include a gas turbine, an electromagnetic motor and the like.

The cylindrical member 4 and the impeller 5 are each formed of a relatively hard material. Examples of such a material include, for example, a resin material and a metallic material. Examples of the resin material include, for example, acrylate resin, polyvinyl chloride (specifically, rigid polyvinyl chloride), polyolefin such as polyethylene, polypropylene, polybutadiene, polysthylene, poly-(4-methylpentene-1), polycarbonate, ABS resin, polymethylmethacrylate (PMMA), polyacetal, polyarylate, polyacrylonitrile, polyvinylidene difluoride, ionomer, acrylonitrile butadiene styrene copolymer, polyester such as polyethylene terephthalate (PET) and polybutylene terephthalate (PBT), butadiene-styrene copolymer, aromatic or aliphatic polyamide, fluorine-based resin such as polytetrafluoroethylene and the like, and the like, and one or two or more of these resin materials may be combined for use. Examples of the metallic material are, for example, pseudoelastic alloy such as Ni—Ti alloy (including super-elastic alloy), shape-memory alloy, stainless steel (for example, all types of SUS such as SUS304, SUS303, SUS316, SUS316L, SUS316J1, SUS316J1L, SUS405, SUS430, SUS434, SUS444, SUS429, SUS430F, SUS302, and the like), cobalt alloy, precious metal such as gold, platinum, tungsten alloy, carbonaceous material (including piano wire) and the like.

The shaft portion 7 preferably has flexibility to an extent which can follow the space in the living body, and has suitable rigidity to allow easy insertion into the living body. In this case, examples of the material which constitutes the shaft portion 7 include a metal and a resin. Examples of the resin include, for example, high-polymer materials such as polyolefin (for example, polyethylene, polypropylene, polybutene, ethylene-propylene copolymer, ethylene-vinyl acetate copolymer, ionomer, mixture of two or more of these components or the like), polyvinyl chloride, polyamide, polyamide elastomer, polyester, polyester elastomer, polyurethane, polyurethane elastomer, polyimide, fluorine-based resin or the like, or a mixture of two or more of these materials, or two or more of the above-described high-polymer materials. Examples of the metal include metals which can be applied to the cylindrical member 4 and the impeller 5 described above. A composite material of metals and resins described above (for example, a multilayer tube or the like including a metal and a resin stacked on top of another) may be applied to the shaft portion 7. In addition, for example, a round wire coil or a flat wire coil formed by knitting an SUS wire, or a twisted wire rope may also be applied. A torque coil formed of thin multi-line multi-layer SUS coil may be used.

Even if not specifically described in this specification, respective members of the above-described medical device assembly 1 may be formed by applying known materials as needed.

The above-described medical device assembly 1 is operated as follows.

As illustrated in FIG. 4, when the drive unit 3 applies a drive force to the impeller 5, the impeller 5 rotates and generates a fluid flow from the distal side toward the proximal side of the cylindrical member 4 (e.g., see arrow A of FIG. 4). The fluid flow toward the proximal side of the cylindrical member 4 is guided by the inclined portion 433 of the wall portion 43, and changes the direction to move towards the outer peripheral side and towards the distal side of the cylindrical member 4 (e.g., see arrow B of FIG. 4). The fluid guided by the inclined portion 433 is discharged from the discharge ports 44 located in the side wall of the cylindrical member 4 and adjacent to the inclined portion 433. The discharged fluid moves to the distal side along the outer peripheral surface of the cylindrical member 4 while maintaining the direction guided by the inclined portion 433 (e.g., see arrow C of FIG. 4). Once the fluid moves to the distal side, the fluid is sucked into the inner cavity 41 of the cylindrical member 4 again through the suction port 42 by the flow formed by the impeller 5 (e.g., see arrow D of FIG. 4). The medical device assembly 1 is thus capable of forming the circulating flow passing through the cylindrical member 4 by rotating the impeller 5.

Generation of the circulating flow passing through the cylindrical member 4 as described above is significantly relevant to the existence of the inclined portion 433 as described above in a flow channel especially for the fluid for moving from the impeller 5 to the discharge ports 44 (i.e., the inclined portion 433 allows the circulating fluid flow).

By using the circulating flow formed in this manner, target solid objects within the living body may be sucked together with the fluid, and collected by the filter 6 in the space 41A of the inner cavity 41 of the cylindrical member 4. In this case, the solid objects may be collected by the filter 6 even though the diameter is relatively small, so that a reliable collection is achieved. Since the solid objects are collected in the space 41A of the inner cavity 41 of the cylindrical member 4, a plurality of solid objects may be collected at the same time by using the medical device assembly 1. Therefore, the number of times of inserting and removing the medical device assembly 1 into and from the living body may be reduced, thereby lowering surgical operation time and reducing the burden on the operator and the patient.

In addition, unlike the basket catheter of the related art, the solid objects can be collected by suction even though the solid objects and the medical device assembly 1 are not in contact with each other. Unlike the basket catheter used in the related art, since the volume of the cylindrical member 4 does not change before or after the collection of the solid objects and the collected solid objects are not exposed from the cylindrical member 4, a risk that the cylindrical member 4 cannot pass the access sheath or the like after having collected the solid objects is avoided (i.e., the medical device assembly 1 may be safely removed from the body). Since the collected solid objects are not exposed through a gap between the structures such as a gripping wire or the like at the time of collection, the inner cavity wall and the living tissue of the living body are prevented from becoming damaged by the exposed end surfaces of the collected objects (e.g., solid objects).

Since the medical device assembly 1 is capable of forming the circulating flow as described above, at the time of suction in narrow portions of the body, the fluid can always be supplied to the narrow portions. Accordingly, sucking in the narrow portions may be continuously performed with the medical device assembly 1 without depletion of the fluid.

Examples of the narrow portions include, for example, ureter, renal calyx, (minor calyces and narrow portions near the minor calyces, in the vicinity of the renal papilla), and in the interior of the ureteral access sheath and the like.

In addition, since the medical device assembly 1 is capable of forming the circulating flow as described above, a higher suction force is achieved at the same number of rotations of the impeller 5 in comparison with the case where the circulating flow is not formed. Accordingly, the size of the impeller 5 may be reduced to a relatively compact size, so that a ratio of the space 41A in the inner cavity 41 to the size of the inner cavity 41 may be increased, allowing a larger amount of the solid objects to be collected. In the case where a relatively compact impeller 5 is employed, the medical device assembly 1 including the cylindrical member 4 may be reduced in size. By using the circulating flow, even when the impeller 5 is relatively compact, suction is achieved with a relatively small number of rotations, and a risk of generation of friction heat between the impeller 5 and the cylindrical member 4 may be reduced, and the durability of the impeller 5, the drive shaft 71 and the like may also be improved.

As described above, with the medical device 1, solid objects having small diameters in a living body and solid objects existing in narrow portions in the living body may be collected and also a plurality of the solid objects may be collected efficiently.

Figure 5A:
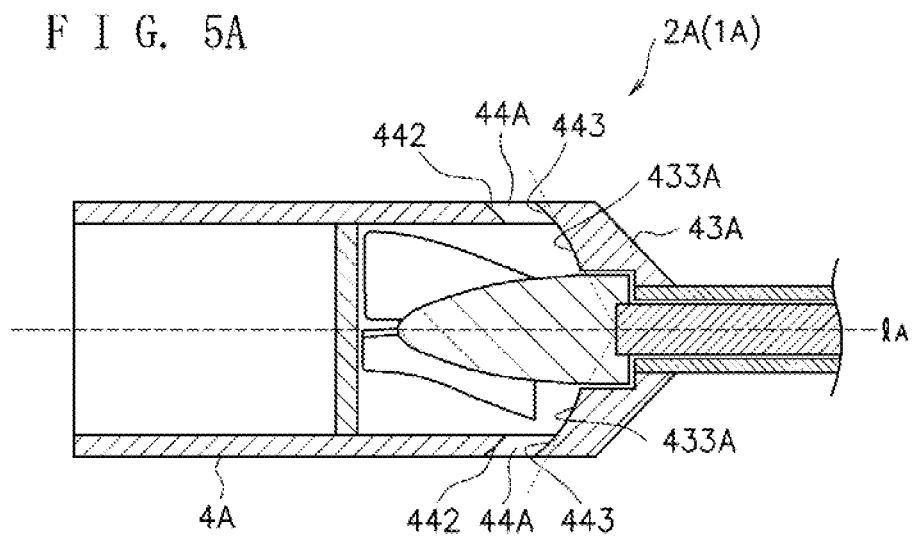
FIGS. 5A and 5B are cross-sectional views of the medical device provided in the medical device assembly according to another modification of the invention.
Figure 5B:
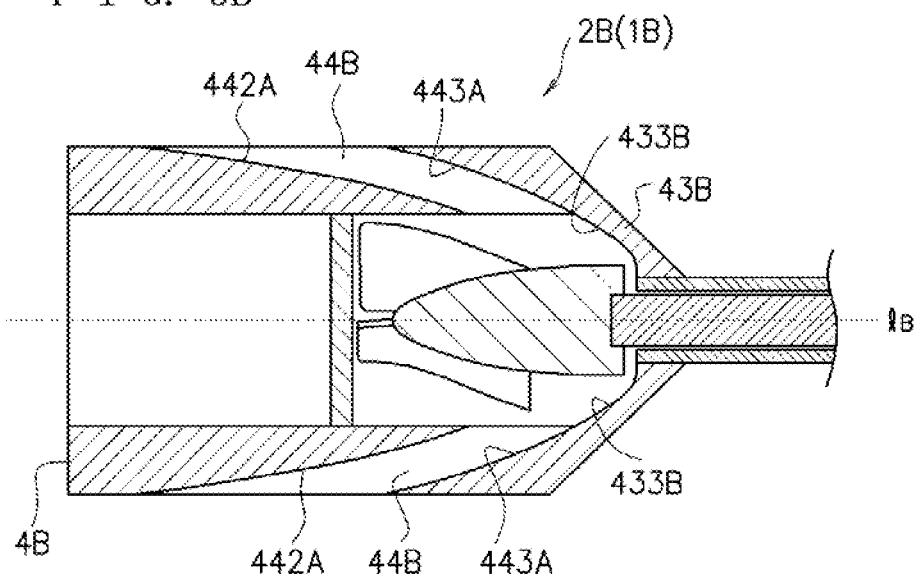
Figure 6A:
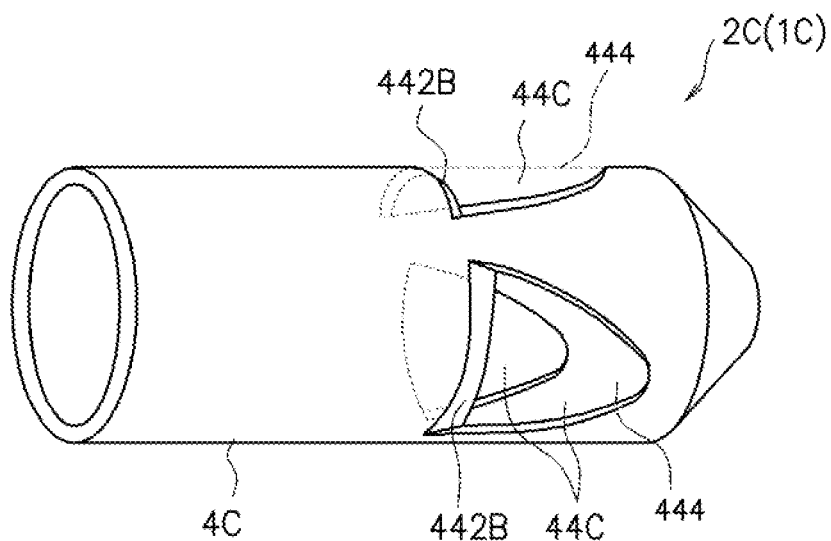
FIG. 6A is a perspective view of a cylindrical member provided in the medical device assembly according to another modification of the invention.
Figure 6B:
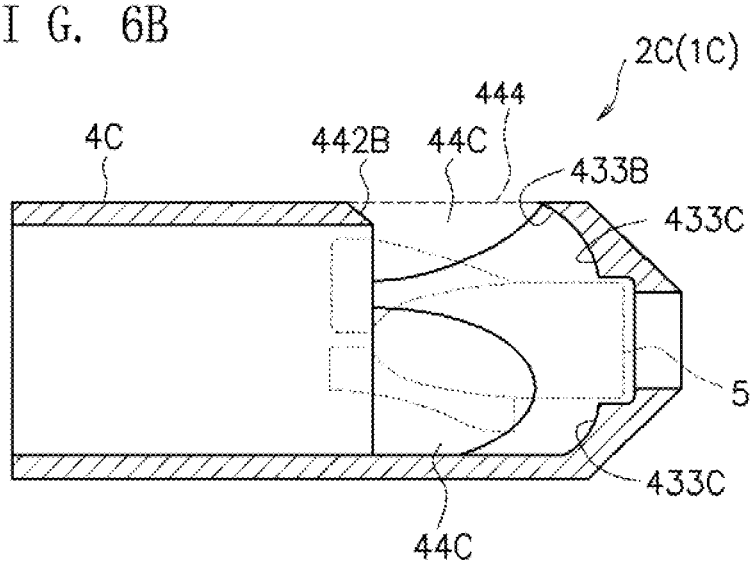
FIG. 6B is a cross-sectional view of the cylindrical member illustrated in FIG. 6A.

Modifications of the above-described medical device assembly 1 include, for example, those in which the configuration of the discharge ports of the cylindrical member is changed as illustrated in FIG. 5A, FIG. 5B, FIG. 6A, and FIG. 6B. FIGS. 5A and 5B are cross-sectional views of the medical device 2A, 2B provided in the medical device assembly according to modifications of the invention. FIG. 6A is a perspective view of a cylindrical member 4C provided in the medical device assembly according to another modification of the invention, and FIG. 6B is a cross-sectional view of the cylindrical member 4C illustrated in FIG. 6A. In the respective drawings, the same components as those in the medical device assembly 1 are denoted by the same reference numerals. In the drawings, components which have been discussed above are omitted as needed. In the descriptions about the modifications given below, different points from the above-described embodiment are mainly described, and the same descriptions are omitted.

In a medical device 2A of a medical device assembly 1A illustrated in FIG. 5A, side walls 442 on a distal side and side walls 443 on a proximal side of discharge ports 44A are inclined from a center axis $l_A$ of a cylindrical member 4A toward the distal side with respect to a transverse direction of the cylindrical member 4A, so that the inner wall surface forms an acute angle with respect to the center axis of the cylindrical member. In this manner, with the side walls 442 and the side walls 443 of the discharge ports 44A inclined toward the distal side, a fluid flow discharged from the discharge ports 44A can be directed reliably toward the distal side, so that formation of the circulating flow is further ensured.

In particular, the side walls 443 on the proximal end side of the medical device assembly 1A are integral with an inclined portion 433A of a wall portion 43A to form an identical plane (i.e., formed out of one piece and with a uniform curvature). Accordingly, the fluid flow guided by the inclined portion 433A can be smoothly guided by the side walls 443, so that the formation of the circulating flow is further ensured.

In a medical device 2B of a medical device assembly 1B illustrated in FIG. 5B, the thickness of a cylindrical member 4B is large, and side walls 442A on a distal side and side walls 443A over the circumferential direction on a proximal side of discharge ports 44B are inclined from a center axis $l_B$ of the cylindrical member 4B toward the distal side with respect to a transverse direction of the cylindrical member 4B. The side walls 442A of the discharge ports 44B are arranged across from the filter 6 in the axial direction up to a portion in the vicinity of the distal end of the cylindrical member 4B. In contrast, the sides wall 443A on the proximal side are formed integrally with an inclined portion 433B of a wall portion 43B to form the identical plane, and are formed so as to extend along the side walls 442A.

Accordingly, the wall portion 44B formed by including the side wall 442A and the side wall 443A can guide a flow channel (i.e., a fluid flow path) to a portion in the vicinity of the distal end. Accordingly, the fluid flow can be smoothly guided to the distal side of the cylindrical member 4B, so that the formation of the circulating flow is further ensured.

In a medical device 2C of a medical device assembly 1C illustrated in FIG. 6A and FIG. 6B, in a side surface of a cylindrical member 4C, three discharge ports 44C are arranged equidistantly in the circumferential direction. Openings 444 on the outer surface side of the cylindrical member 4C of the respective discharge ports 44C are formed so that the width on the distal end in the circumferential direction of the cylindrical member 4C is larger than the width on the proximal end. More specifically, the width of the openings 444 in the circumferential direction is continuously increased from the proximal end toward the distal end. Accordingly, a flow formed by the impeller 5 and guided by an inclined portion 433C and flowing toward the distal end of the cylindrical member 4 is more readily discharged from the discharge ports 44C (i.e., fluid flowing in a more distal direction travels through a wider opening than fluid flowing less distally). Accordingly, the discharged fluid can be transferred reliably to the distal side of the cylindrical member 4C, so that the formation of the circulating flow is further ensured.

A side wall 442B on the distal side and a side wall 443B on the proximal side of the discharge ports 44C are inclined over the circumferential direction from a center axis of the cylindrical member 4C toward the distal side with respect to the transverse direction of the cylindrical member 4C. Furthermore, the side wall 443B on the proximal side is integrated with the inclined portion 433C of the wall portion 43C to form an identical plane.

In addition to the illustrated modifications as described above, examples of modifications in which the configuration of the discharge port is modified include, for example, those in which the number of the discharge ports is changed. In the illustrated embodiment and modifications, three discharge ports have been described. However, the invention is not limited to three discharge ports, and, for example, could include one to twenty discharge ports. Preferably, three to six discharge ports are included.

In modifications changing the configuration of the discharge ports, the positions of the discharge ports in the axial direction may be changed from one discharge port to another. For example, in the case where a plurality of the discharge ports are included, a row of discharge ports may be on the distal end of the cylindrical member 4 and a row of discharge ports may be on the proximal end of the cylindrical member, and discharge ports located at different positions in the axial direction are arranged alternately.

In modifications changing the configuration of the discharge ports, the shapes of the plurality of discharge ports may be differentiated from one discharge port to another.

Other modifications of the medical device assembly 1 described above include, for example, those in which the configuration of the impeller is changed. In the medical device assembly 1 described above, the impeller 5 has been described as a screw. However, the medical device disclosed here is not limited to possessing a screw impeller, and the impeller may be a paddle type, a turbine type, a ribbon type, and the like as needed.

The size and the design may be changed as needed in the respective kinds of the impellers.

For example, in the case where the impeller is the propeller-type screw, the number of the blades may be 2 to 10, preferably 3 to 6. The angle of the blades may be 36° to 180°, and preferably, from 60° to 120°.

The above-described embodiments and modifications may be combined as needed as long as there is no inconsistency in configuration.

A method of the invention will be described on the basis of preferred embodiments.

Figure 8A:
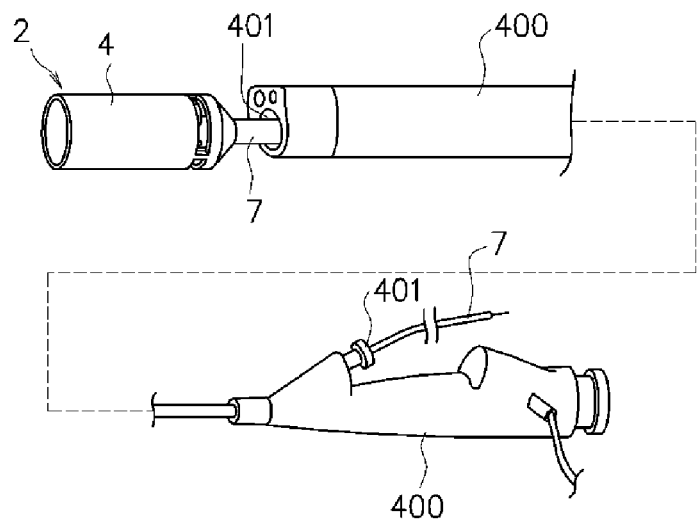
FIGS. 8A and 8B are schematic drawings illustrating an example of a method of assembling the medical device assembly illustrated in FIG. 1.
Figure 8B:
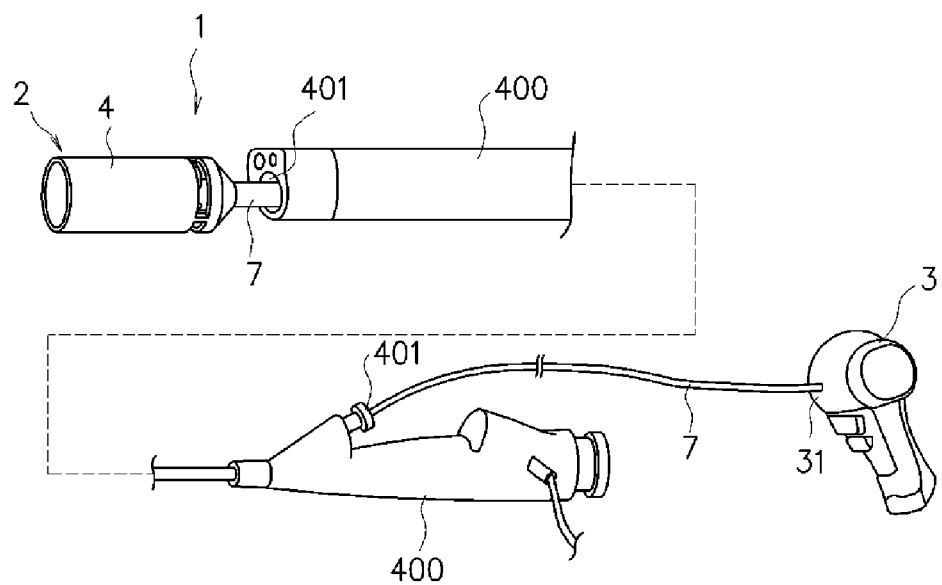

FIGS. 7A to 7D are explanatory schematic drawings of the preferred embodiment of the method of the invention, and FIGS. 8A and 8B are schematic drawings illustrating an example of a method of assembling the medical device assembly illustrated in FIG. 1. In the relevant drawings, the components may be illustrated at different ratios from the actual size ratios to partly enlarge or reduce the component sizes for the purpose of explanation of this embodiment.

The method disclosed here is a method of collecting an existing solid object together with a fluid in a living body, including: inserting a medical device into the living body, the medical device comprising:
   a cylindrical member comprising an inner wall surface and an inner cavity, the inner cavity possessing a distal end and a proximal end, the cylindrical member further comprising a suction port and a discharge port, and the cylindrical member possessing a central axis;
   an impeller in the inner cavity,
   a filter in the inner cavity, and
   an inclined inner wall surface being inclined from the center axis of the cylindrical member toward the distal end of the inner cavity with respect to a transverse direction of the cylindrical member so that the part of the inner wall surface forms an acute angle with the center axis of the cylindrical member;
   moving the medical device within the living body so that the suction port is near the solid object;
   activating the impeller to create a fluid flow channel from the suction port to the discharge port of the cylindrical member, the fluid in the fluid flow channel being inducted through the induction port, conveyed proximally to contact the inclined inner wall surface, and redirected by the inclined inner wall to exit the discharge port so that the fluid is moving toward the distal end of the inner cavity;
   sucking the solid object together with the fluid into the inner cavity; and
   collecting the solid object by using the filter.

The method of the invention may be used for collecting any solid object in the living body and, for example, an object in any respective portions in the living body as described above. However, the method will be described for the therapy of the urinary tract stone disease. Therefore, the applicable portions in the living body are in a urinary tract (for example, ureter, urethra, kidney (renal pelvis, renal calyx), bladder), and the objects to be collected are calculi such as urinary tract stones, bladder stones, urethra stones or the like, or broken calculus pieces of the calculi.

Therefore, the method of this embodiment includes inserting a hard renal pelvis urethroscope into a urinary tract, and inserting a ureteral access sheath into the urinary tract prior to the respective steps described above, and then inserting a ureter stent into the urinary tract after the respective steps described above.

The respective steps are described below.

In the first step of the method of this embodiment, the hard renal pelvis urethroscope is inserted into the urinary tract. Insertion of the hard renal pelvis urethroscope into the urinary tract is achieved by using a cystoscope which is generally used in the medical field, inserting a guide wire which is widely known in the medical field into the ureter or renal pelvis and renal calyx via the urethra and the bladder, and inserting the hard renal pelvis urethroscope into the urinary tract along the guide wire. By inserting the hard renal pelvis urethroscope into the urinary tract in this manner, the urinary tract can be monitored, the symptom can be easily determined, the urinary tract can be expanded, and insertion of a ureteral access sheath 200, which will be described later, is facilitated.

While the hard renal pelvis urethroscope is inserted, the calculi is broken up as much as possible and collected as needed, if desired. Breaking of the calculus may be achieved by irradiating with laser such as Ho:YAG laser or the like, and collection of the calculi and broken pieces is achieved by using a known basket catheter.

When this step is terminated, the hard renal pelvis urethroscope is removed from the body. However, the guide wire is preferably indwelled in the ureter for the next step (i.e., the guide wire remains indwelled when the urethroscope is removed from the body).

In the next step, the ureteral access sheath 200 is inserted into a urinary tract 100 (FIG. 7A). For example, the ureter and the renal pelvis and renal calyx correspond to the urinary tract 100. Accordingly, the medical device assembly 1 may be fed easily to a portion in the vicinity of a position in the urinary tract 100 where intended (i.e., target) calculi 300 exist. In this embodiment, the calculi 300 are described as including the calculi and broken calculus pieces.

Insertion of the ureteral access sheath 200 into the urinary tract is achieved by inserting the ureteral access sheath 200 along the indwelled guide wire. After the insertion of the ureteral access sheath 200, the guide wire may be pulled out. In the case where the calculi 300 have a relatively large size which makes the calculi 300 difficult to pass through the ureteral access sheath, the calculi 300 are broken into a relatively small size by using the braking device such as Ho:YAG laser or the like together with a soft renal pelvis urethroscope 400.

In the following step, the medical device assembly is provided.

The medical device assembly may be of any one of those described above. However, in this embodiment, the medical device assembly 1 described above is used as the medical device assembly.

The medical device assembly 1 includes the medical device 2 and the drive unit 3 combined to each other (i.e., connected). However, it is preferable to further combine the soft renal pelvis urethroscope 400. Accordingly, removal of the calculi 300 is achieved while monitoring an affected area.

The cylindrical member 4 of the medical device 2 may be larger than the smallest diameter of an instrument channel 401 of the soft renal pelvis urethroscope 400, and hence may not be able to pass through the instrument channel 401. In this case, as illustrated in FIG. 8A and FIG. 8B, a proximal side of the shaft portion 7 of the medical device 2 is inserted into a distal side of a channel 401 and is passed to a proximal side of a channel 401, and then the proximal side of the shaft portion 7 is connected to the drive unit 3, so that the medical device assembly 1 including the soft renal pelvis urethroscope 400 may be assembled.

The provided medical device assembly 1 may be subjected to cleaning and sterilized by a known method as needed.

This step may be performed before or after the two steps described above.

In the next step, the medical device assembly 1 is inserted into the ureter 200, and the suction port 42 is arranged in the vicinity of the calculi 300 (FIG. 7B).

In this embodiment, insertion of the medical device assembly 1 is achieved via the ureteral access sheath 200.

In the next step, the impeller 5 is activated to suck the calculi 300 into the inner cavity 41 of the cylindrical member 4 together with the fluid to collect the calculi 300 by using the filter 6 (FIG. 7C and FIG. 7D).

Specifically, a drive force is generated by the drive unit 3 and the drive force is applied to the impeller 5 via the drive shaft 71 to rotate the impeller 5. When the impeller is rotated, a circulating flow passing through the cylindrical member 4 is generated by the above-described mechanism, whereby suction of the fluid and the calculi 300 from the suction port 42 is enabled. The fluid is discharged from the discharge ports 44, while the calculi 300 are captured by the filter 6.

In the suction using the circulating flow as described above, the calculi 300 are collected by being attracted by the circulating flow (i.e., the circulating fluid flow moves the calculi 300 into the suction port 42). Therefore, the calculi 300 which are not in contact with the medical device assembly 1 or the calculi 300 having a relatively small diameter which can hardly be gripped by a basket catheter can be collected by the medical device assembly 1. Since a plurality of calculi 300 can be collected, the number of times of removing and inserting the medical device assembly 1 into and out of the living body may be reduced, so that the surgical operation time may be reduced and the burden on the operator and the patient may be reduced.

When performing suction in narrow portions in the body, the medical device assembly 1 is capable of always supplying the fluid to the narrow portions by circulating the fluid flow as described above, which allows the fluid to always be supplied to the narrow portions.

In the case where the fluid for circulating is not sufficient in the affected area, the fluid may be supplied as needed to the affected area. For example, in this embodiment, liquid such as saline, perfusate or the like may be supplied to the affected area. A reservoir containing solution (e.g., an infusion bag containing saline, perfusate, or the like) may be connected to the proximal side of the instrument channel 401 of the soft renal pelvis urethroscope 400 to supplement the fluid from the distal side of the instrument channel 401 via the inner cavity of the instrument channel. Specifically, a three-way cock is connected to the proximal side of the instrument channel 401, the shaft portion 7 of the medical device assembly 1 is passed through one of channels of the three-way cock, and an infusion solution line connected to a saline bag is connected to the other channel of the three-way cock may be used.

The calculi 300 which are collected once in the cylindrical member 4 may be discharged to the outside of the body by pulling out the medical device assembly 1 including the cylindrical member 4 from the inside of the body.

Removal of the medical device assembly 1 is preferably performed while the circulating flow is generated by activating the impeller 5. Accordingly, the state in which the calculi 300 are sucked is maintained, and dropping out of the calculi from the cylindrical member 4 is prevented.

By repeating insertion, activation, and pulling out of the medical device assembly 1, removal of the calculi from the inside of the body is achieved.

A portion where the calculi 300 are removed from the cylindrical member 4 may be within the bladder. In addition, for the purpose of changing the positions of the calculi 300 (repositioning), the calculi 300 may be taken into the cylindrical member 4 in a renal calyx within the renal pelvis and renal calyx and be released in another renal calyx.

In the final step, the ureter stent is indwelled in the ureter. Indwelling may be performed after having pulled out the medical device assembly 1 and the ureteral access sheath 200. In this step, first the guide wire is introduced into the ureter or the renal pelvis and renal calyx via the urethra and the bladder. In addition, an indwelling ureter stent for the upper ureter is indwelled so as to cover the guide wire, and then the guide wire is pulled out. The ureter stent is used for preventing an evanescent blockage of the ureter or the like after the operation. The ureter stent is removed after a predetermined number of days are elapsed.

The method of using the medical device disclosed here is not limited to the above description, and the medical device assembly 1 may be used together with the hard renal pelvis urethroscope, for example. In other words, in the operation including the monitoring with the hard renal pelvis urethroscope, breakup of the stones, and extraction of the stones to be performed prior to the operation of extraction of the stone with the soft renal pelvis urethroscope 400, the medical device assembly 1 may be used instead of the basket catheter.

Although the medical device, medical device assembly and method of using the medical device disclosed here have been described in conjunction with the illustrated embodiments, the invention is not limited to the disclosed embodiments.

In the invention, the respective configurations may be replaced by those which can provide the same function, or an arbitrary configuration may be added.

The detailed description above describes a medical device, a medical device assembly and a method for using a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for collecting a solid object in a living body, the medical device comprising:
a cylindrical member possessing a center axis, an inner wall surface that defines a flow channel, and a side wall, the cylindrical member having an inner cavity possessing a distal end and a proximal end, a suction port on the distal end of the inner cavity, and a discharge port in the side wall configured to communicate with the inner cavity;
an impeller in the inner cavity configured to carry fluid from the suction port to the discharge port;
a filter in the inner cavity configured to collect the solid object, the filter comprising a plurality of through holes configured to allow the fluid to pass through the filter and to prevent the solid object from passing through the filter to thereby collect the solid object in the inner cavity distal of the filter, the filter being at least one of a textile fabric, a mesh, or a porous film; and
at least part of the inner wall surface, which defines the flow channel allowing a movement of the fluid from the impeller to the discharge port, is inclined from the center axis of the cylindrical member toward the distal end with respect to a transverse direction of the cylindrical member so that the part of the inner wall surface forms an acute angle with the center axis of the cylindrical member.

2. The medical device according to claim 1, wherein the impeller comprises blades,
the cylindrical member includes a proximal wall portion traversing the inner cavity proximally of a proximal end of the blades of the impeller, and
the proximal wall portion is inclined from the center axis of the cylindrical member toward the distal end with respect to the transverse direction of the cylindrical member.

3. The medical device according to claim 2, wherein the proximal wall portion and part of the side wall which possesses the discharge port are integrated and form an identical plane.

4. The medical device according to claim 3, wherein at least part of the side wall is inclined from the center axis of the cylindrical member toward a far end side with respect to the transverse direction of the cylindrical member.

5. The medical device according to claim 1, wherein an opening of the discharge port on an outer surface side of the cylindrical member has a width in a circumferential direction of the cylindrical member on the distal end of the opening that is larger than a width on a proximal end of the opening.

6. The medical device according to claim 1, wherein the impeller comprises blades, and
an opening of the discharge port on the inner cavity side faces a proximal end of the blades of the impeller.

7. The medical device according to claim 1, wherein the impeller is a screw.

8. The medical device according to claim 1, wherein the medical device is configured to move a fluid discharged from the discharge port in a direction toward the distal end of the cylindrical member to form a circulating flow passing back to the suction port and through the inner cavity during the operation of the impeller.

9. The medical device according to claim 1, wherein
the impeller comprises an impeller blade, the impeller blade possessing a proximal-most end;
the discharge port is an opening with a proximal end and a distal end; and
the proximal-most end of the impeller blade is positioned between the distal end and the proximal end of the opening in an axial direction of the cylindrical member.

10. The medical device according to claim 1, wherein the filter is disc-shaped.

11. A medical device for collecting a solid object in a living body, the medical device comprising:
a cylindrical member possessing a center axis, an inner wall surface that defines a flow channel, and a side wall, the cylindrical member having an inner cavity possessing a distal end and a proximal end, a suction port on the distal end of the inner cavity, and a discharge port in the side wall configured to communicate with the inner cavity;
an impeller in the inner cavity configured to carry fluid from the suction port to the discharge port;
a filter in the inner cavity configured to collect the solid object, the filter comprising a plurality of through holes configured to allow the fluid to pass through the filter and to prevent the solid object from passing through the filter to thereby collect the solid object in the inner cavity distal of the filter; and
at least part of the inner wall surface, which defines the flow channel allowing a movement of the fluid from the impeller to the discharge port, is inclined from the center axis of the cylindrical member toward the distal end with respect to a transverse direction of the cylindrical member so that the part of the inner wall surface forms an acute angle with the center axis of the cylindrical member, wherein the filter is a meshed fabric possessing uniformly sized openings.

12. A medical device assembly for collecting a solid object in a living body together with a fluid in the living body, the medical device assembly comprising:

a cylindrical member possessing a center axis, an inner wall surface that defines a flow channel of the fluid, and a side wall, the cylindrical member having an inner cavity possessing a distal end and a proximal end, a suction port on the distal end of the inner cavity, and a discharge port in the side wall and configured to communicate with the inner cavity, the discharge port in the side wall possessing a proximal-most end;

an impeller in the inner cavity configured to carry the fluid from the suction port to the discharge port;

a filter in the inner cavity configured to collect the solid object;

at least part of the inner wall surface, which defines a flow channel allowing a movement of the fluid from the impeller to the discharge port, being inclined from a center axis of the cylindrical member toward a distal end with respect to a transverse direction of the cylindrical member so that the part of the inner wall surface forms an acute angle with the center axis of the cylindrical member, the inclined part of the inner wall surface possessing a distal-most end; and the distal-most end of the inclined part of the inner wall surface being located at the proximal-most end of the discharge port.

13. The medical device assembly according to claim 12, wherein the impeller comprises blades;

the cylindrical member includes a proximal wall portion traversing the inner cavity proximally of a proximal end of the blades of the impeller, and the proximal wall portion is inclined from the center axis of the cylindrical member toward the distal end with respect to the transverse direction of the cylindrical member.

14. The medical device assembly according to claim 13, wherein the proximal wall portion and part of the side wall which possesses the discharge port are integrated and form an identical plane.

15. The medical device according to claim 12, wherein the impeller comprises an impeller blade, the impeller blade possessing a proximal-most end;

the discharge port is an opening with a proximal end and a distal end; and the proximal-most end of the impeller blade is positioned between the distal end and the proximal end of the opening in an axial direction of the cylindrical member.

16. The medical device assembly according to claim 12, further comprising:

a drive shaft coupled to the impeller and configured to transmit a drive force to the impeller to rotate the impeller; and a drive unit coupled to the drive shaft and configured to rotate the drive shaft by applying the drive force.

17. The medical device assembly according to claim 12, wherein the filter is positioned in the inner cavity distal to the impeller to partition to the inner cavity into a collecting chamber and an impeller chamber, the impeller being in the impeller chamber and the solid object being configured to be collected in the collecting chamber; and the flow channel of the fluid being from the suction port through the filter to the impeller and then out of the discharge port so that the solid object is configured to be collected in the collecting chamber by the filter preventing the solid object from passing therethrough while the fluid flows through the filter.

18. A method of collecting a solid object in a living body together with a fluid in the living body, the method comprising:

inserting a medical device into the living body, the medical device comprising: a cylindrical member comprising an inner wall surface and an inner cavity, the inner cavity possessing a distal end and a proximal end, the cylindrical member further comprising a suction port and a discharge port, and the cylindrical member possessing a central axis; an impeller in the inner cavity; a filter in the inner cavity, and an inclined inner wall surface inclined from the center axis of the cylindrical member toward the distal end of the inner cavity with respect to a transverse direction of the cylindrical member so that the part of the inner wall surface forms an acute angle with the center axis of the cylindrical member, the filter being positioned distally of the impeller within the inner cavity to partition the inner cavity into a distal space distal to the filter and a proximal space proximal to the filter;

moving the medical device within the living body so that the suction port is positioned near the solid object;

activating the impeller to create a fluid flow channel from the suction port to the discharge port of the cylindrical member, the fluid in the fluid flow channel being inducted through the induction port, conveyed proximally to contact the inclined inner wall surface, and redirected by the inclined inner wall to exit the discharge port so that the fluid is moving toward the distal end of the inner cavity;

sucking the solid object together with the fluid into the inner cavity; and collecting the solid object using the filter, the collecting of the solid object comprises retaining the solid object in the distal space while the fluid flows through the filter.

19. The method according to claim 18, further comprising a step of introducing additional fluid into the living body.

20. The method according to claim 19, wherein the impeller is activated to create the fluid flow channel while removing the medical device from the living body.

21. The method according to claim 18, wherein the cylindrical member possesses a side wall, and the discharge port is located in the side wall.

22. The method according to claim 18, comprising removing the medical device from the living body with the solid object in the distal space of the inner cavity of the cylindrical member.

23. The method according to claim 18, wherein the impeller comprises blades, the cylindrical member includes a proximal wall portion traversing the inner cavity proximally of a proximal end of the blades of the impeller, and the proximal wall portion is inclined from the center axis of the cylindrical member toward the distal end with respect to the transverse direction of the cylindrical member.

* * * * *